US009016287B2

United States Patent
Nibbe

(10) Patent No.: US 9,016,287 B2
(45) Date of Patent: Apr. 28, 2015

(54) DENTAL FLOSSING DEVICE

(71) Applicant: Ash Nibbe, Grand Rapids, MI (US)

(72) Inventor: Ash Nibbe, Grand Rapids, MI (US)

( * ) Notice: Subject to any disclaimer, the term of this patent is extended or adjusted under 35 U.S.C. 154(b) by 0 days.

(21) Appl. No.: 14/206,966

(22) Filed: Mar. 12, 2014

(65) Prior Publication Data

US 2014/0261511 A1  Sep. 18, 2014

Related U.S. Application Data

(60) Provisional application No. 61/799,823, filed on Mar. 15, 2013.

(51) Int. Cl.
*A45D 7/00* (2006.01)
*A61C 15/00* (2006.01)
*A61C 15/04* (2006.01)

(52) U.S. Cl.
CPC .................................. *A61C 15/046* (2013.01)

(58) Field of Classification Search
CPC ...... A61C 15/00; A61C 15/02; A61C 15/041; A61C 15/043; A61C 15/046; A61C 15/047; A61C 15/048
USPC .......... 132/321–329, 309, 200; 433/146, 147, 433/141, 134, 82, 89
See application file for complete search history.

(56) References Cited

U.S. PATENT DOCUMENTS

| | | | | |
|---|---|---|---|---|
| 2,187,442 | A * | 1/1940 | Beach | 132/326 |
| 3,311,116 | A * | 3/1967 | Foster | 132/326 |
| 3,799,177 | A * | 3/1974 | Bragg | 132/326 |
| 3,870,059 | A * | 3/1975 | Bennington | 132/325 |
| 3,901,251 | A * | 8/1975 | Johnston | 132/325 |
| 4,050,470 | A | 9/1977 | Miller | |
| 4,495,957 | A * | 1/1985 | Beggs et al. | 132/325 |
| 4,920,993 | A * | 5/1990 | Mackie | 132/324 |
| 4,926,820 | A | 5/1990 | Wearn | |
| 5,060,681 | A * | 10/1991 | Westbrook et al. | 132/325 |
| 5,105,840 | A | 4/1992 | Giacopuzzi | |
| 5,199,452 | A * | 4/1993 | Cheng | 132/325 |
| 5,503,168 | A * | 4/1996 | Wang | 132/324 |
| 5,560,378 | A * | 10/1996 | Tiphonnet | 132/325 |
| 5,570,710 | A | 11/1996 | Wei et al. | |
| 5,573,022 | A | 11/1996 | Winters | |
| 5,680,875 | A * | 10/1997 | Winters | 132/324 |
| 5,692,532 | A * | 12/1997 | Gabrovsek | 132/325 |
| 6,131,586 | A * | 10/2000 | Flanagan | 132/325 |
| 6,363,949 | B1 * | 4/2002 | Brown | 132/325 |
| 7,305,997 | B2 * | 12/2007 | Liu et al. | 132/325 |
| 7,464,716 | B1 * | 12/2008 | Nygren, Jr. | 132/322 |
| 8,042,556 | B2 * | 10/2011 | Bowsher | 132/323 |
| 8,146,608 | B2 | 4/2012 | Chung | |
| 8,596,286 | B2 * | 12/2013 | Bornstein et al. | 132/323 |
| 2005/0092347 | A1 * | 5/2005 | Fan | 132/325 |
| 2006/0011212 | A1 * | 1/2006 | Achepohl et al. | 132/325 |
| 2008/0289648 | A1 | 11/2008 | Liu | |

* cited by examiner

*Primary Examiner* — Vanitha Elgart
(74) *Attorney, Agent, or Firm* — Cochran Freund & Young LLC

(57) ABSTRACT

Disclosed is a dental flossing device in which dental floss is strung between a dispensing side handle, which dispenses dental floss, and goes into a receiving side handle, which receives used dental floss.

2 Claims, 15 Drawing Sheets

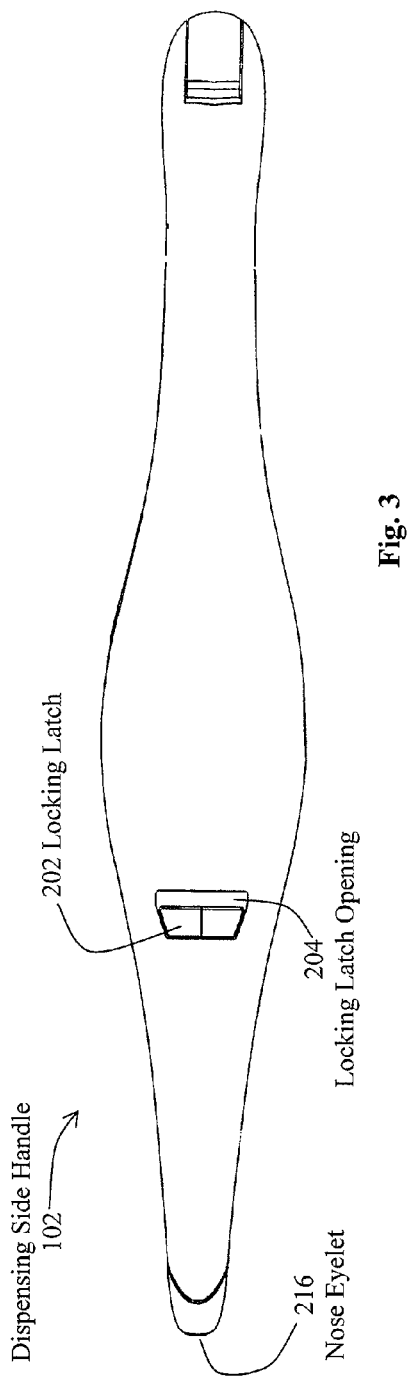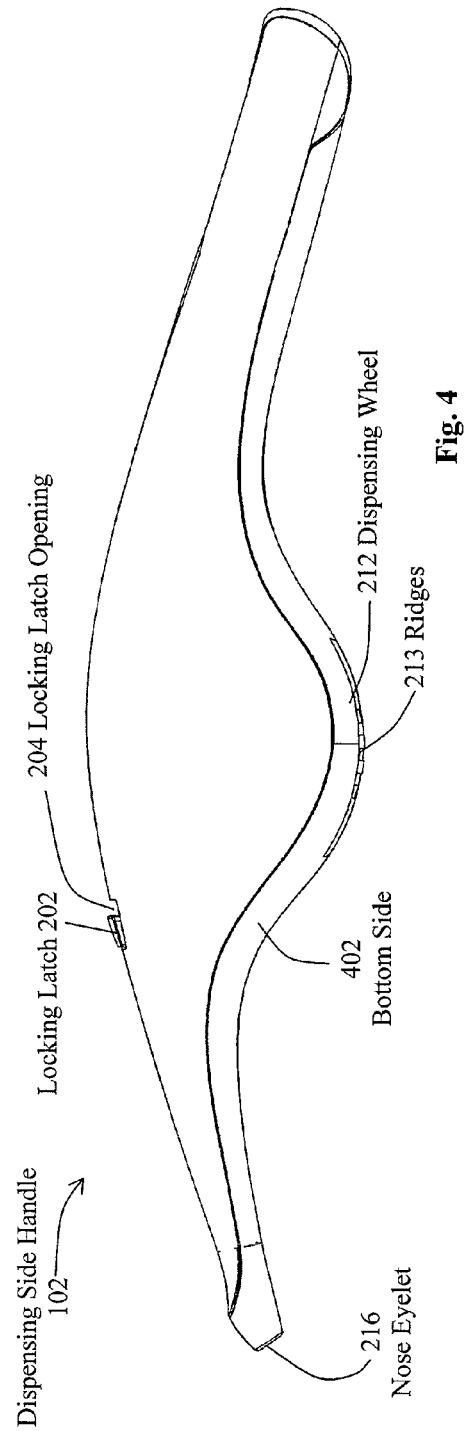

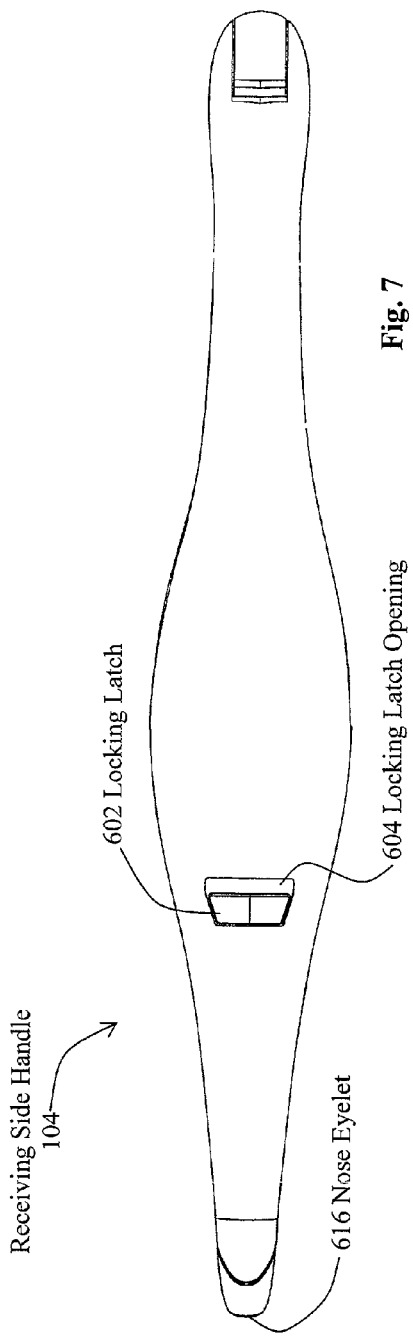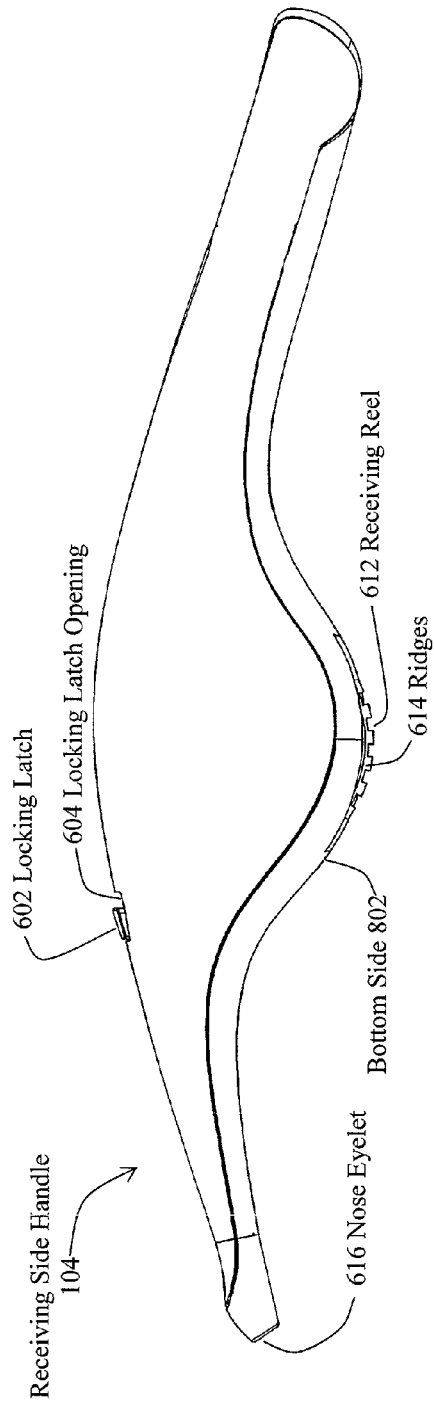
Fig. 7
Fig. 8

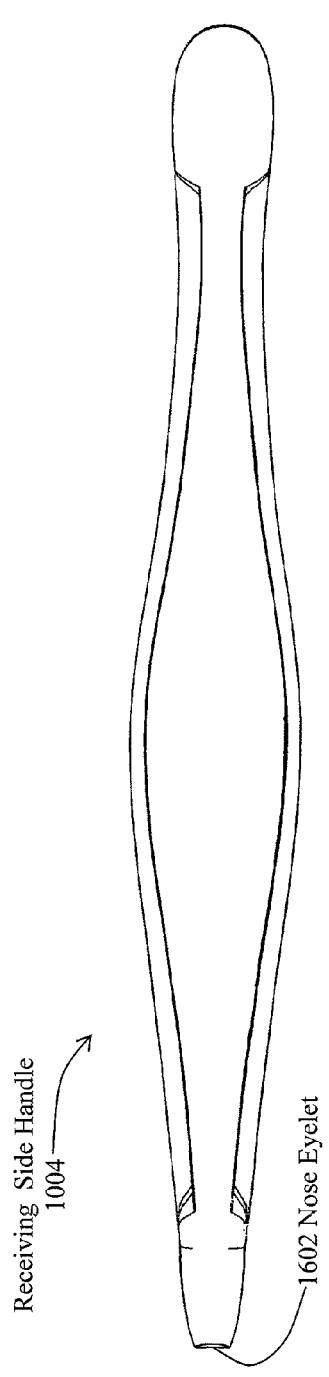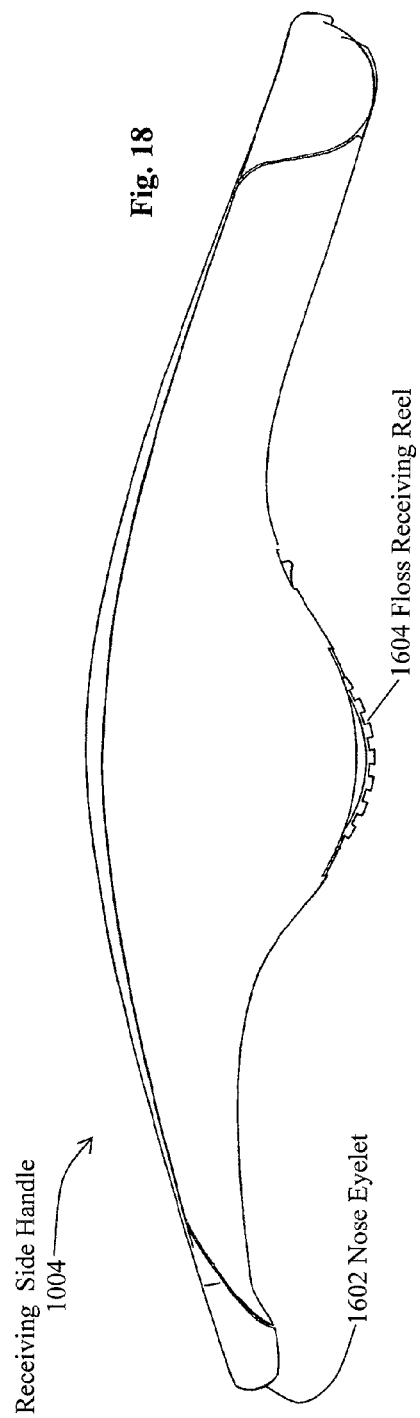

DENTAL FLOSSING DEVICE

CROSS-REFERENCE TO RELATED APPLICATION

This application is a non-provisional application of U.S. Patent Application Ser. No. 61/799,823, entitled "Dental Flossing Device," filed by Ash Nibbe on Mar. 15, 2013. The entire contents of the above mentioned application are hereby specifically incorporated herein by reference for all they disclose and teach.

BACKGROUND

Dental flossing is an important part of dental hygiene. Dental flossing is more likely if an individual has a mechanism so that flossing is simple, easy and not very time-consuming.

SUMMARY

An embodiment of the present invention may comprise a method of using a teeth flosser comprising: providing a dispensing side handle that dispenses dental floss; providing a receiving side handle that receives the dental floss; providing a dispensing wheel having ridges, the dispensing wheel protruding from a bottom of the dispensing side and the ridges creating friction on the bottom of the dispensing side so that the dispensing wheel cannot rotate without rotational force applied to the dispensing wheel; placing a spool of dental floss onto a spool pin that is part of the dispensing wheel; threading the dental floss through a dispensing nose eyelet so that an end of the dental floss easily exits the dispensing nose eyelet; latching a dispensing cover of the dispensing side handle by engaging a locking latch in a locking latch opening; threading the end of the dental floss into a receiving nose eyelet on the receiving side handle and placing the dental floss on a slot having a floss receiving reel; rotating the floss receiving reel so that the dental floss wraps around the floss receiving reel; latching a receiving cover of the receiving side handle by engaging a locking latch on the receiving side handle into a locking latch opening on the receiving side handle; rotating both the dispensing wheel and the receiving reel while flossing the teeth so that the dental floss travels from the dispensing side to the receiving side; depressing the locking latch on the receiving side from the locking latch opening from the receiving side so that the receiving cover is opened; depressing the locking latch on the dispensing side from the locking latch opening on the dispensing side to open the dispensing top cover; pulling the dental floss from the receiving side so that the dental floss is cut on a floss cutter on the dispensing side; engaging the locking latch on the receiving side into the locking latch opening so that the receiving cover is closed on the receiving side, engaging the locking latch on the dispensing side into the locking latch opening so that the dispensing cover is closed on the dispensing side.

An embodiment of the present invention may further comprise a method of flossing teeth comprising: providing a dispensing side handle that dispenses dental floss; providing a receiving side handle that receives the dental floss; providing an upper jaw having upper teeth on the dispensing side handle; providing a lower jaw having lower teeth on the dispensing side handle; disposing a spool of floss in an open pocket of the dispensing side handle; threading an end of the dental floss over the lower teeth through a floss channel having ribs and the end of the dental floss exiting at a dispensing nose eyelet; closing a dispensing cover by engaging a locking latch on the dispensing side into a locking latch on the dispensing side; providing an upper finger depression above the upper jaw located on the dispensing cover; providing a lower finger depression under the lower jaw on the dispensing side so that when force is applied to the upper finger depression and the lower finger depression on the dispensing side handle, the upper teeth and the lower teeth create a tension on the dental floss; threading the end of the dental floss into a receiving nose eyelet; securing the end of the dental floss into a slot located on a floss receiving reel; rotating the floss receiving reel so that the dental floss wraps around the floss receiving reel; closing a receiving cover by engaging a locking latch on the receiving side into a locking latch opening on the receiving side; advancing the dental floss while flossing the teeth by releasing pressure on the upper finger depression and the lower finger depression on the dispensing side so that the floss is not under tension on the dispensing side handle while rotating the floss receiving reel so that the floss is retained in the floss receiving reel; depressing the locking latch on the receiving side from the locking latch opening on the receiving side to open the receiving cover; hooking the dental floss along the floss cutter of the receiving side, so that the dental floss is cut; engaging the locking latch on the receiving side into the locking latch so that the receiving cover is closed on the receiving side handle.

An embodiment of the present invention may further comprise a device for flossing teeth comprising: a dispensing side handle that dispenses dental floss; a receiving side handle that receives the dental floss; a dispensing wheel having ridges so that the dispensing wheel protrudes from a bottom of the dispensing side handle and the ridges create friction on the bottom of the dispensing side handle, so that the dispensing wheel cannot move without rotational force applied to the dispensing wheel; a spool pin that is part of the dispensing wheel that can receive a spool of dental floss; a dispensing nose eyelet through which the dental floss is threaded, so that the end of the dental floss easily exits the dispensing nose eyelet; a dispensing cover having a locking latch, so that when closed the locking latch engages into a locking latch opening; a receiving nose eyelet through which the dental floss is threaded on the receiving side; a floss receiving reel having a slot, so that the dental floss is disposed in the slot and the floss receiving reel is rotated so that the dental floss wraps around the floss receiving reel; a receiving cover that is closed by engaging a locking latch on the receiving side into a locking latch opening on the receiving side, so that while rotating both the dispensing wheel and the receiving reel while flossing the teeth, the dental floss travels from the dispensing side to the receiving side; a floss cutter on the dispensing side handle so that, when the receiving cover is opened and the dental floss is pulled out of the receiving nose eyelet, the dispensing cover is opened and the dental floss from the receiving side handle can be cut on the floss cutter and both the dispensing cover and the receiving cover can be closed.

An embodiment of the present invention may further comprise a device for flossing teeth comprising: a dispensing side handle that dispenses dental floss; a receiving side handle that receives the dental floss; an upper jaw having upper teeth on the dispensing side handle; a lower jaw having lower teeth on the dispensing side handle, so that there is an open pocket adjacent to the lower jaw where a spool of floss can be disposed; ribs that surround the lower teeth that provide a floss channel so that the end of the dental floss is threaded over the lower teeth through the floss channel and the end of the dental floss exits at a dispensing nose eyelet; a dispensing cover that can be closed by engaging a locking latch into a locking latch opening; an upper finger depression above the upper jaw located on the dispensing cover; a lower finger depression under the lower jaw on the dispensing side handle, so that when force is applied to the upper finger depression and the lower finger depression on the dispensing side handle, the upper teeth and the lower teeth create a tension on the dental floss; a receiving nose eyelet through which the dental floss is guided; a slot located on a floss receiving reel so that rotating the floss receiving wheel, will enable the dental floss to wrap around the floss receiving wheel; a receiving cover that will close by engaging a locking latch into a locking latch opening on the receiving side handle to allow the dental floss to be transferred from the dispensing side to the receiving side by releasing pressure on the upper finger depression and the lower finger depression on the dispensing side handle while rotating the floss receiving reel, so that the floss is retained in the receiving reel, and depressing the locking latch on the receiving side handle to disengage the locking latch from the locking latch opening on the receiving side handle to open the receiving cover, so that the dental floss can be cut on the dental floss cutter, and engaging the locking latch on the receiving side handle into the locking latch, so that the receiving cover is closed on the receiving side handle.

BRIEF DESCRIPTION OF THE DRAWINGS

FIG. 3 is a top view of the dispensing side of the handle of FIG. 1.

FIG. 4 is a side view of the dispensing side the handle of FIG. 1.

FIG. 7 is a top view of the receiving side of the handle of FIG. 1.

FIG. 8 is a side view of the receiving side of the handle of FIG. 1.

FIG. 17 is a top view of the receiving side of the handle of FIG. 10.

FIG. 18 is a side view of the receiving side of the handle of FIG. 10.

DETAILED DESCRIPTION OF THE EMBODIMENTS

Figure 1:
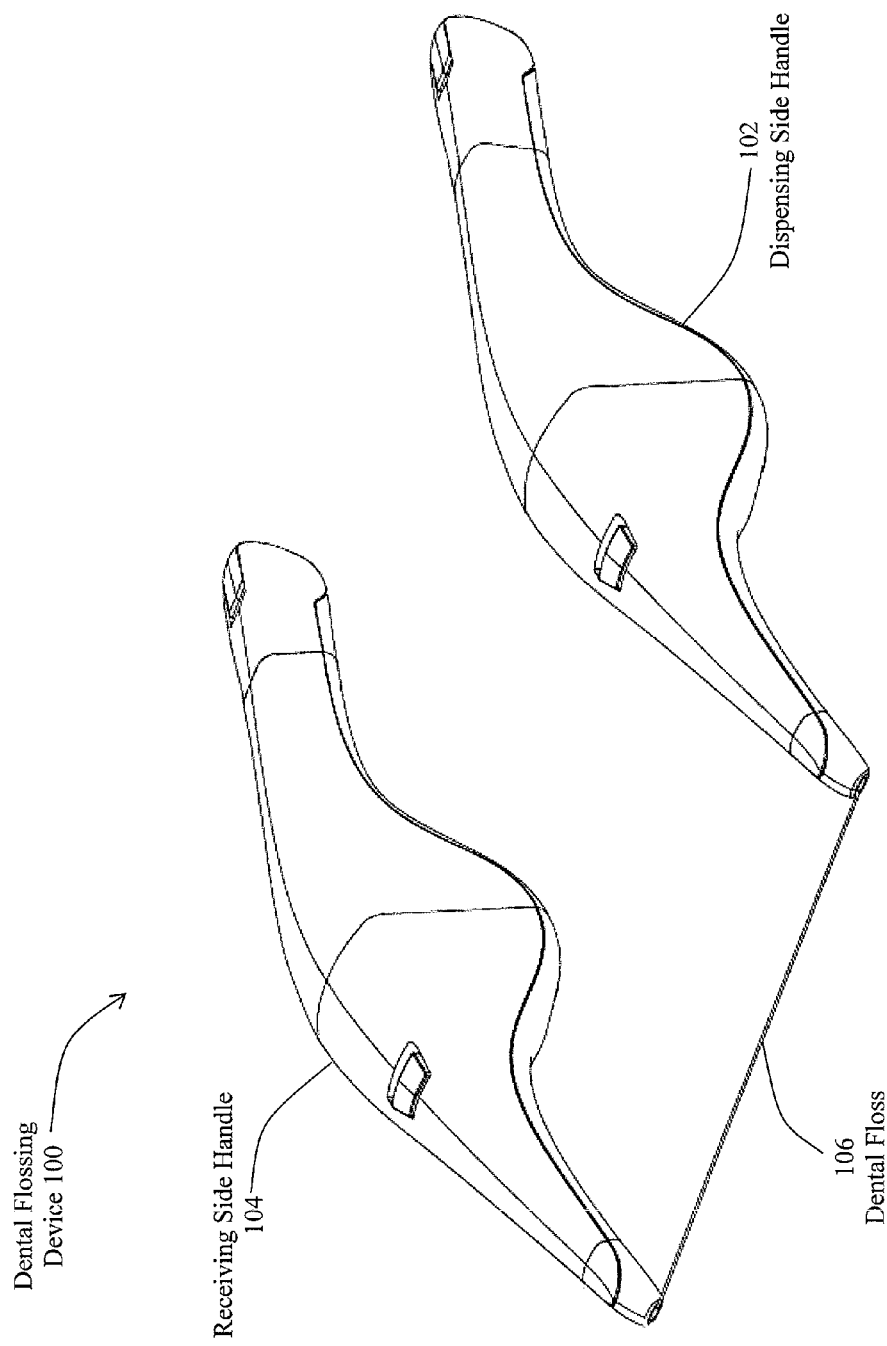
FIG. 1 is an isometric view of an embodiment of a dental flossing device.

FIG. 1 is an isometric side view of an embodiment of a device used for flossing teeth. FIG. 1 shows dental flossing device 100 having a dispensing side handle 102 and a receiving side handle 104, so that dental floss 106 is connected between dispensing side handle 102 and receiving side handle 104. Dispensing side handle 102 and receiving side handle 104 are held by a user in each hand, so that the dental floss 106 is taut between the two handles (dispensing side handle 102 and receiving side handle 104), so that a user may easily floss the user's teeth without having to insert fingers in the user's mouth, or wrap dental floss around the user's fingers. The dispensing side handle 102 dispenses clean, new floss, while the receiving side accepts the used floss, which eliminates debris from teeth flossing from getting on fingers. Both the dispensing side handle 102 and receiving side handle 104 may be opened, so that new floss may be inserted, used floss may be removed, and dental flossing device may be washed or rinsed without causing damage to the internal components of dental flossing device 100.

Figure 2:
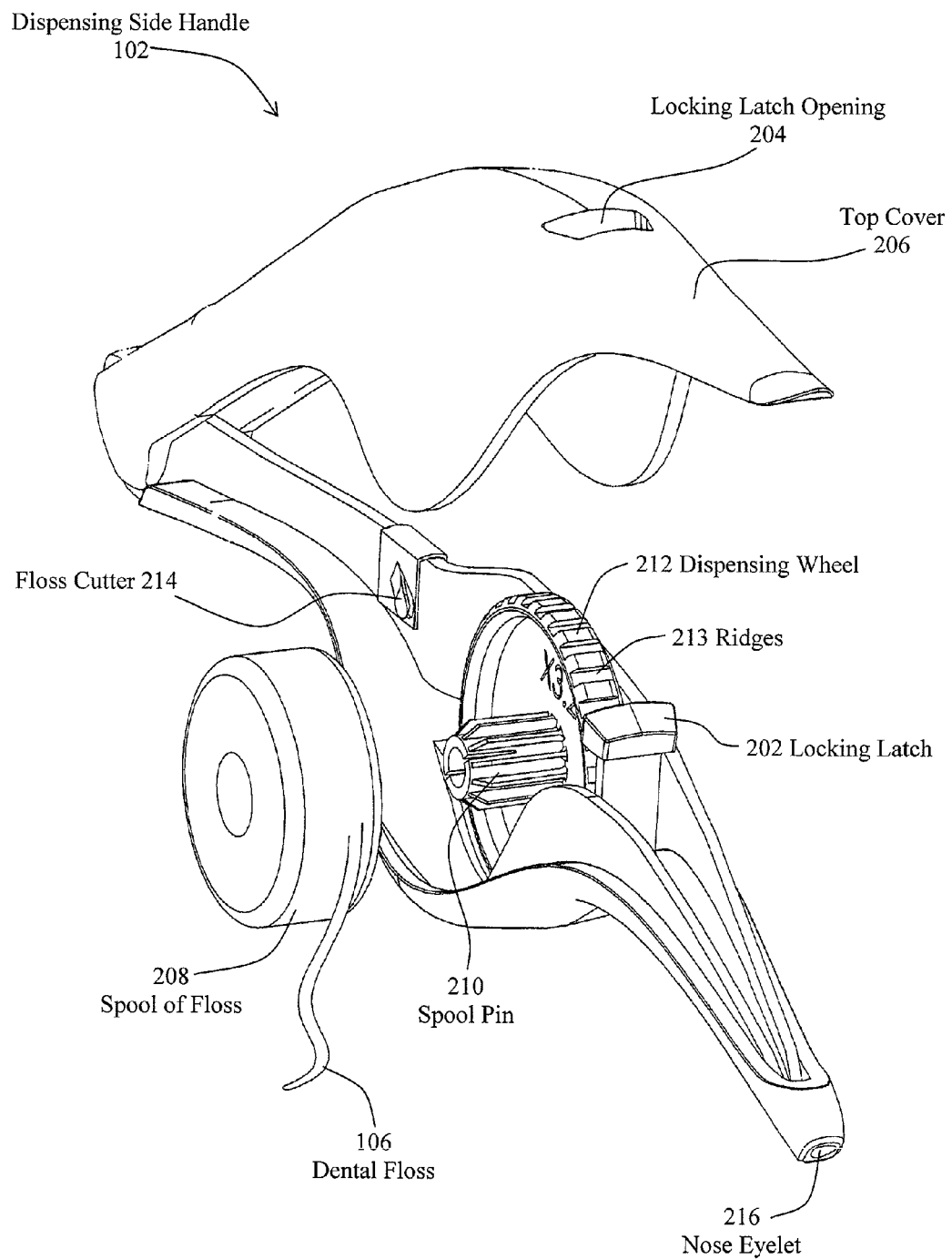
FIG. 2 is an isometric view of the dispensing side of the handle of FIG. 1.

FIG. 2 is an isometric view of dispensing side handle 102 with top cover 206 open, thereby showing the internal elements of dispensing side handle 102. To open dispensing side handle 102, locking latch 202 is disengaged from locking latch opening 204, so that top cover 206 may be opened. A spool of floss 208 can be placed on spool pin 210, which is part of dispensing wheel 212. Dispensing wheel 212 has ridges 213 that project from dispensing wheel 212. Once the spool of floss 208 is disposed on spool pin 210, dental floss 106 is guided through the end of nose eyelet 216. Dispensing side handle 102 also has a floss cutter 214, so that when a person is finished flossing, they are able to open top cover 206 and cut used dental floss 106 from receiving side handle 104 (shown in FIG. 1) with floss cutter 214. Alternatively, the dispensing side handle 102 and receiving side handle 104 can be opened along a lengthwise axis, like a book. If the dispensing side handle 102 and receiving side handle 104 have a straighter design, the opening axis can be made to be straight along the length of both the dispensing side handle 102 and receiving side handle 104. In that case, both the dispensing side handle 102 and the receiving side handle 104 could be opened like a book with the hinged part along the straight lengthwise axis. Such a design would allow easy access to all the internal parts of both the dispensing side handle 102 and receiving side handle 104.

FIG. 3 is a top view of dispensing side handle 102, showing locking latch 202 that is locked onto locking latch opening 204. FIG. 3 also shows a top view of nose eyelet 216.

FIG. 4 is a side view of dispensing side handle 102. FIG. 4 shows nose eyelet 216, dispensing wheel 212, and locking latch 202 through locking latch opening 204. When dispensing wheel 212 is rotated, the dispensing wheel creates friction due to ridges 213 having contact with the bottom side 402 of dispensing side handle 102. The ridges 213 click on bottom side 402, thereby preventing the entire spool of floss (shown in FIG. 2) from freely flowing from the end of nose eyelet 216, which will be more clearly seen in FIG. 5.

Figure 5:
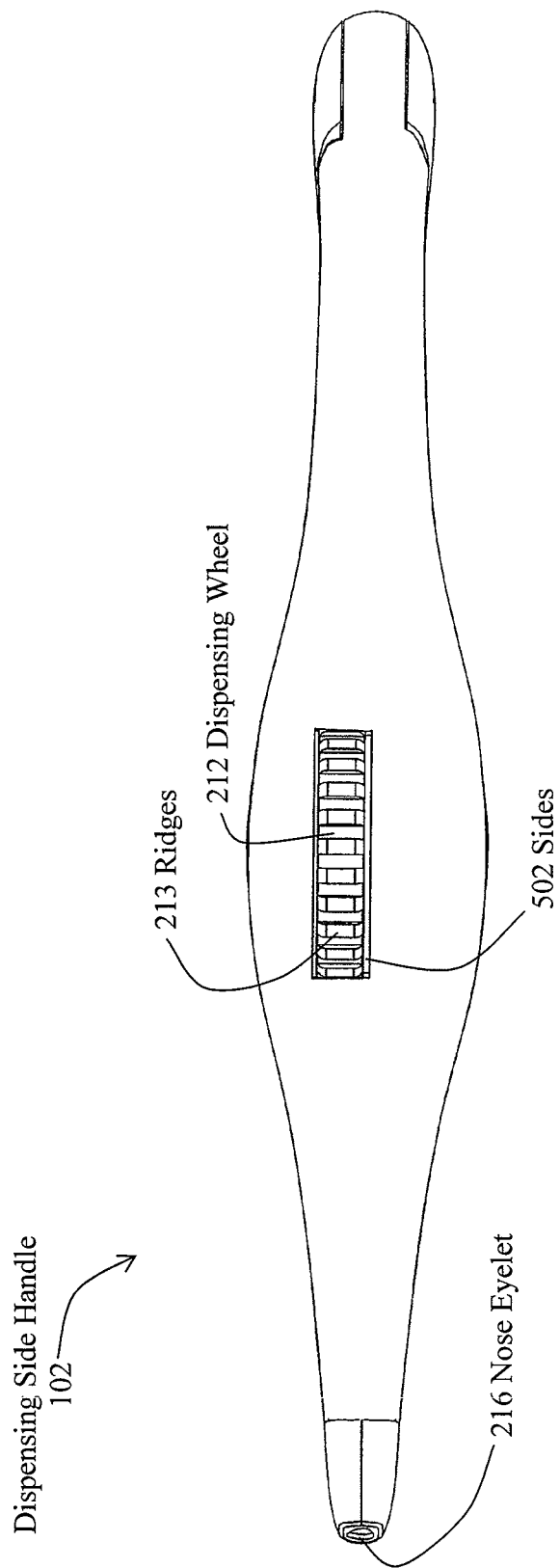
FIG. 5 is a bottom view of the dispensing side of the handle of FIG. 1.

FIG. 5 is a bottom view of dispensing side handle 102 showing nose eyelet 216, dispensing wheel 212 and ridges 213. When dispensing wheel 212 is rotated toward nose eyelet 216, ridges 213 create friction on sides 502, so that spool of floss 208, shown in FIG. 2, does not freely move through nose eyelet 216. In other words, force must be applied to dispensing wheel 212 in a rotational motion so that ridges can overcome the friction on sides 502.

Figure 6:
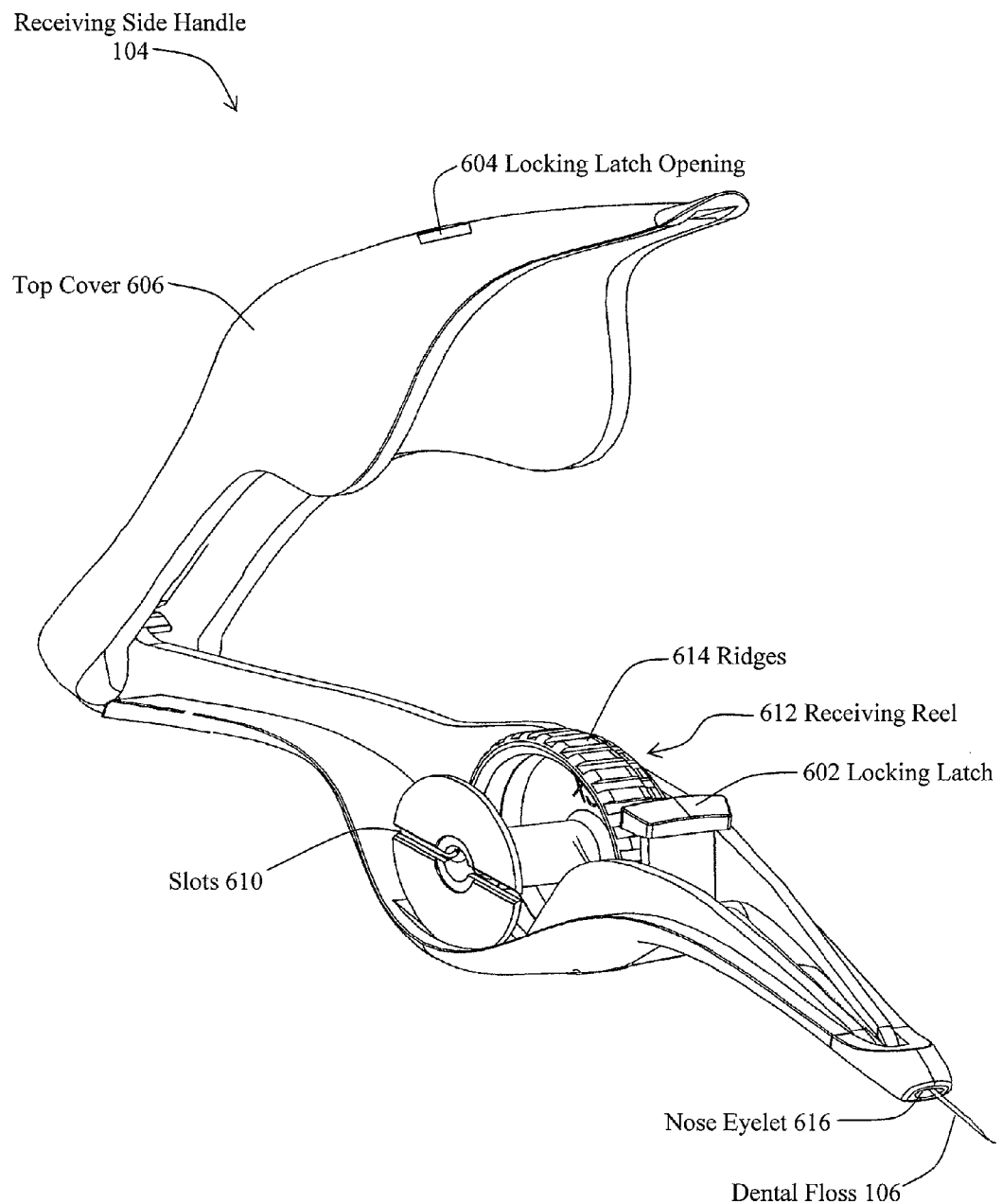
FIG. 6 is an isometric view of the receiving side of the handle of FIG. 1.

FIG. 6 is an isometric view of receiving side handle 104 that was shown in FIG. 1 with top cover 606 open to show the internal components of receiving side handle 104. To open top cover 606, locking latch 602 is depressed so it becomes disengaged from locking latch opening 604. Receiving side handle 104 has a receiving reel 612 that has slots 610 and ridges 614 that are on receiving reel 612. In operation, dental floss 106 is fed through nose eyelet 616, so that dental floss 106 is thread across slot 610 in the receiving reel 612, so that dental floss 106 is wound counterclockwise around receiving reel 612.

FIG. 7 is a top view of receiving side handle 104 that was shown in FIG. 1. Receiving side handle 104 has nose eyelet 616 and locking latch 602 that locks into locking latch opening 604.

FIG. 8 is a side view of receiving side handle 104 that was shown in FIG. 1. Receiving side handle 104 in FIG. 8 shows nose eyelet 616, receiving reel 612, and locking latch 602 that is engaged in lock latch opening 604. When receiving reel 612 is rotated, ridges 614 create friction on bottom side 802, so that receiving reel 612 does not freely rotate without force, thereby preventing the used dental floss to freely move from nose eyelet 616.

Figure 9:
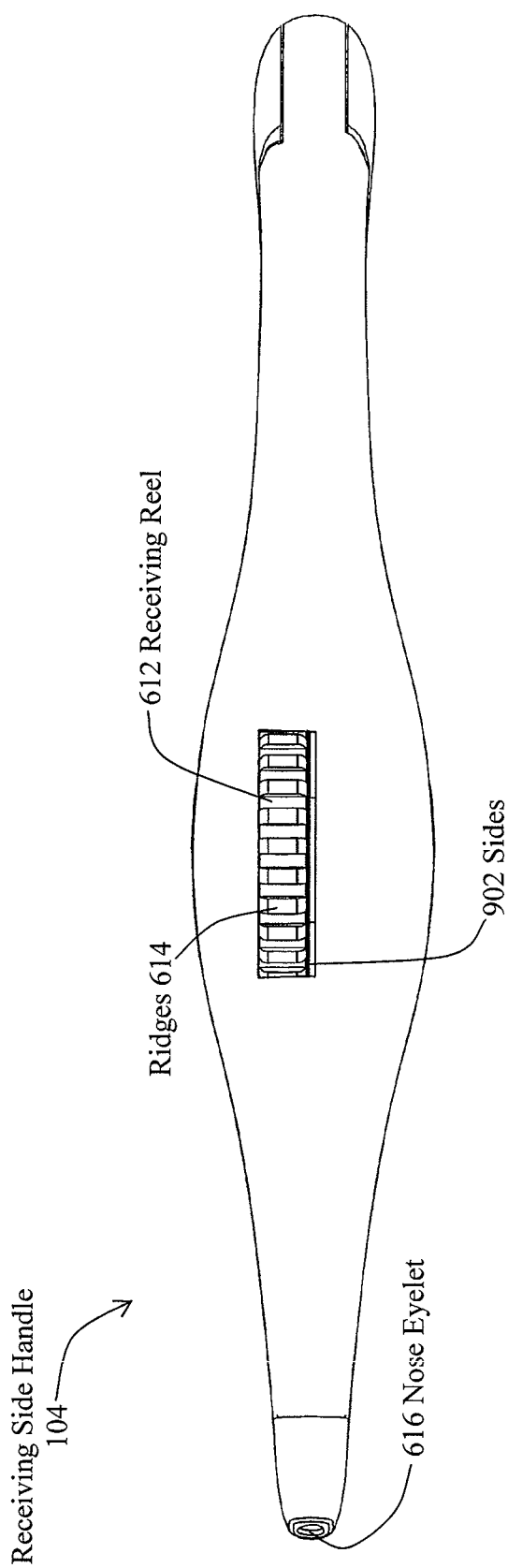
FIG. 9 is a bottom view of the receiving side of the handle of FIG. 1.

FIG. 9 is a bottom view of receiving side handle 104 that was shown in FIG. 1. FIG. 9 shows receiving side handle 104 having nose eyelet 616, receiving reel 612, that has ridges 614, that create friction on sides 902 when rotated toward nose eyelet 616, so that dental floss 106 is prevented from freely exiting nose eyelet 616.

In operation, dental flossing device 100 is used by enabling the user to advance dental floss by rotating dispensing wheel 212, so floss travels through nose eyelet 216, that was shown in FIG. 2, so dental floss 106 is able to advance to receiving side handle 104, that was shown in FIG. 1, and dental floss 106 is retained in receiving reel 612 of receiving side handle 104. In order to dispose of the used dental floss 106 that was wound in receiving reel 612, top cover 606 is removed and dental floss 106 is pulled out of nose eyelet 616. The user can then open dispensing side and cut away the used dental floss 106 by means of floss cutter 214 on dispensing side that was shown in FIG. 2.

Figure 10:
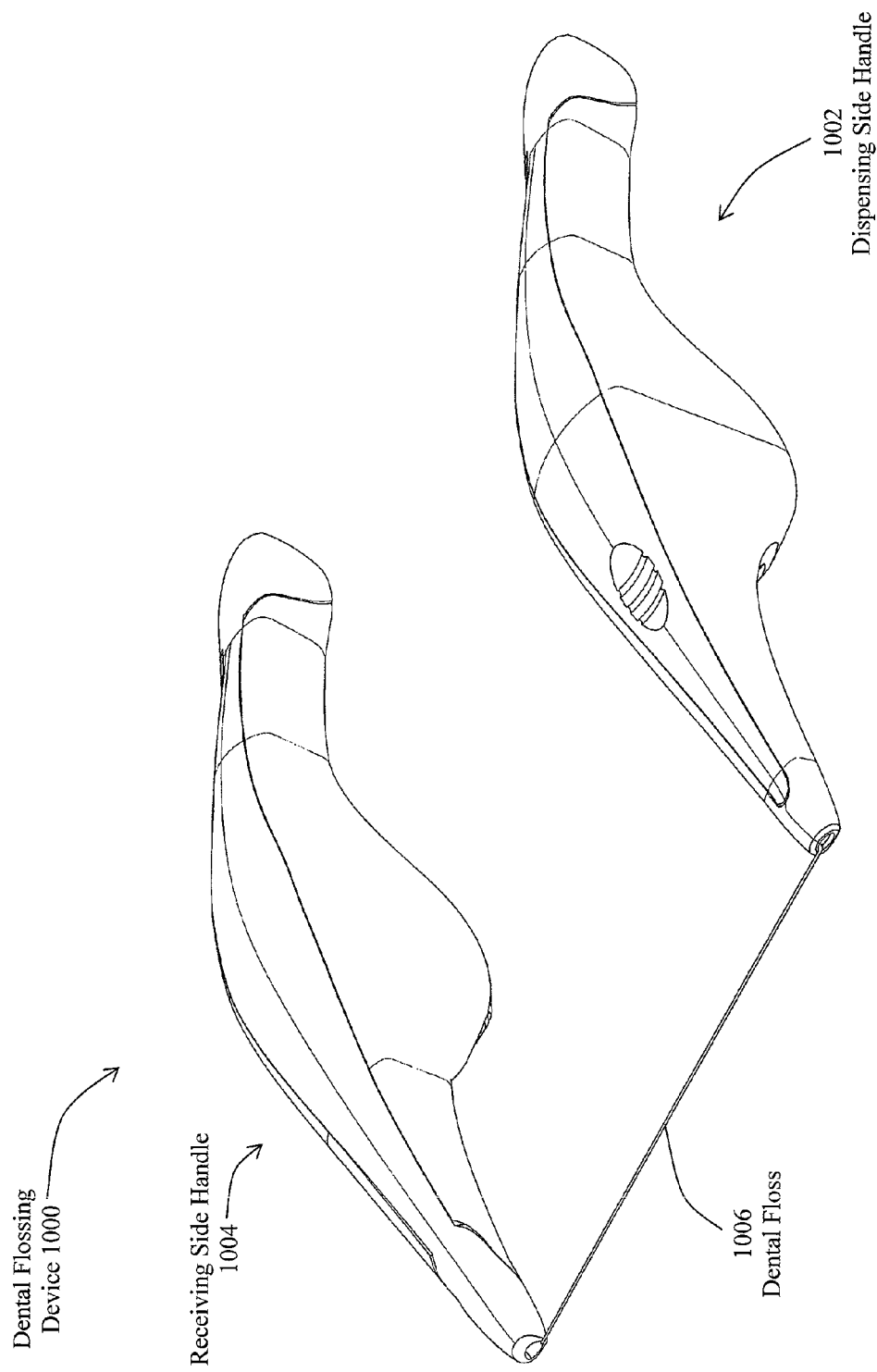
FIG. 10 is another embodiment of a dental flossing device.

FIG. 10 is another embodiment of a device used to floss teeth. FIG. 10 is an isometric view of dental flossing device 1000 having a dispensing side handle 1002 and a receiving side handle 1004 that are connected by dental floss 1006. As in the first embodiment of FIG. 1, both the dispensing side handle 1002 and the receiving side handle 1004 are held by a user, so that the user does not have to insert fingers into their mouth. The embodiment of FIG. 1 keeps dental floss 106 securely retained inside both the receiving side handle 104 and dispensing side handle 102 by receiving reel 612 and dispensing wheel 212. The embodiment of FIG. 10 retains the used dental floss 1006 in a similar manner using a receiving reel 1604, which will be discussed later. However, the dispensing side handle 1002 of the embodiment of FIG. 10 prevents the dental floss from freely moving from nose eyelet 1126 by applying force to an upper finger depression 1118 and a lower finger depression 1120, which will be shown and discussed in FIG. 11.

Figure 11:
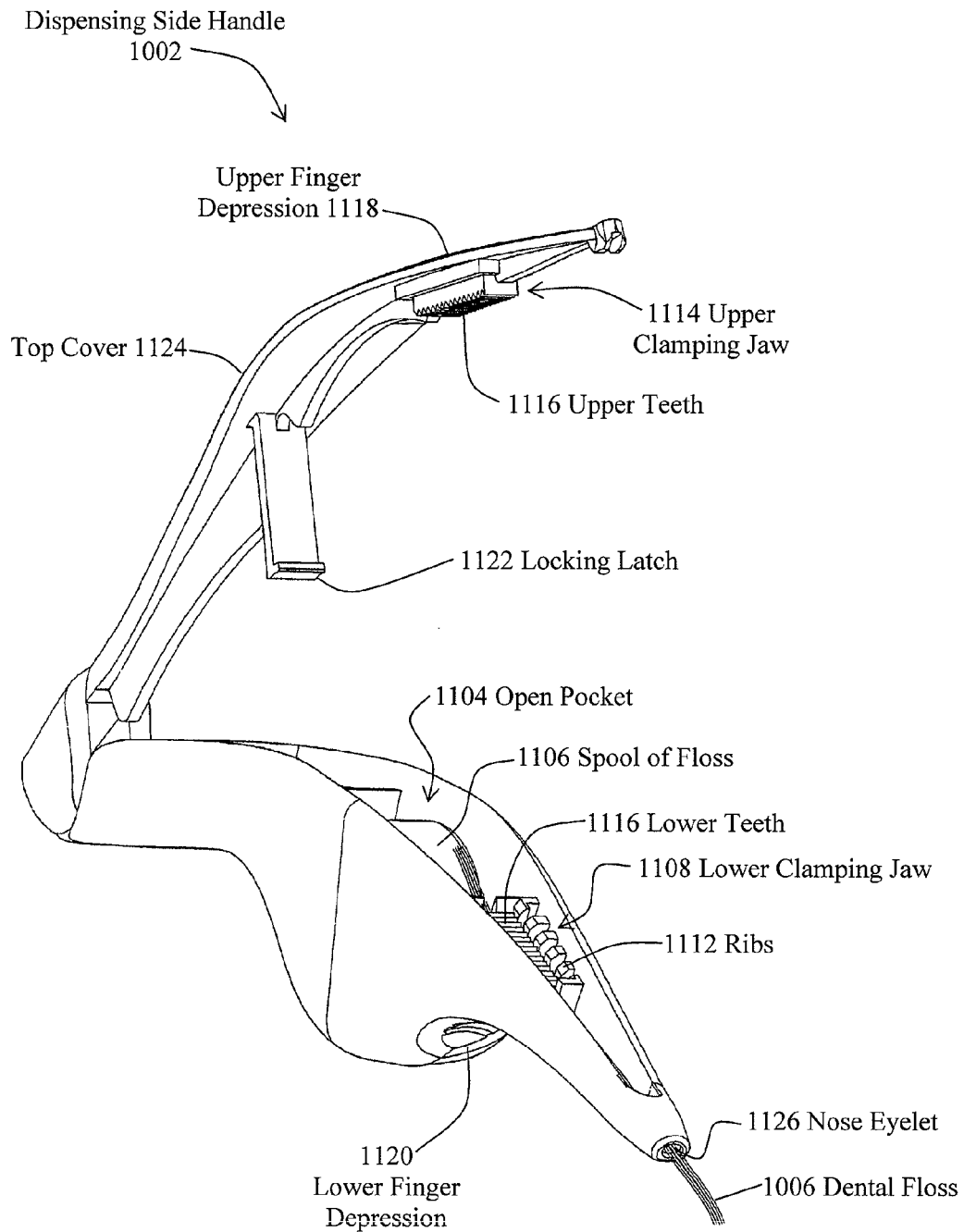
FIG. 11 is an isometric view of the dispensing side of the handle of FIG. 10.

FIG. 11 is an isometric view of dispensing side handle 1002 that was shown in FIG. 10. FIG. 11 shows dispensing side handle 1002 that has top cover 1124 open, so that the internal components of dispensing side handle 1002 are shown. Top cover 1124 is opened by depressing locking latch 1122 from a lower area of dispensing side handle 1002. Dispensing side handle 1002 has open pocket 1104, so that spool of floss 1106 may be dropped into open pocket 1104, then dental floss 1006 passes over lower teeth 1110 of lower clamping jaw 1108, then dental floss 1006 exits through nose eyelet 1126. Dispensing side handle 1002 has an upper clamping jaw 1114 and a lower clamping jaw 1118 that, when pressed together, upper teeth 1116 and lower teeth 1110 create tension on dental floss 1006. Ribs 1112, located on lower clamping jaw 1108, create a foundation for lower teeth 1110 and also assist in uniting upper clamping jaw 1114 and lower clamping jaw 1118. Friction is created on dental floss 1006 when force is applied to both lower finger depression 1120 and upper finger depression 1118, thereby preventing dental floss 1006 from freely flowing from nose eyelet 1126.

Figure 12:
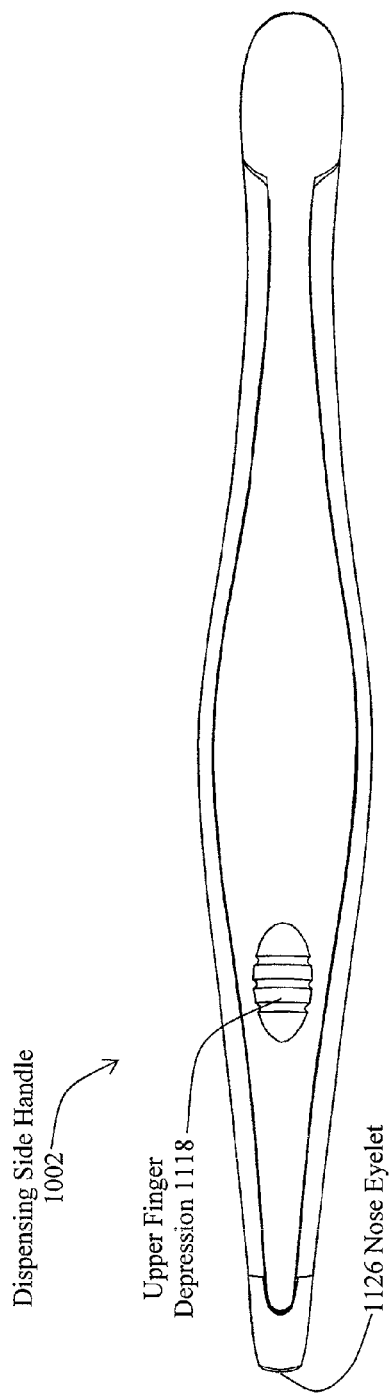
FIG. 12 is a top view of the dispensing side of the handle of FIG. 10.

FIG. 12 is a top view of dispensing side handle 1002 that was shown in FIG. 10. Dispensing side handle 1002, in FIG. 12, shows upper finger depression 1118 and nose eyelet 1126.

Figure 13:
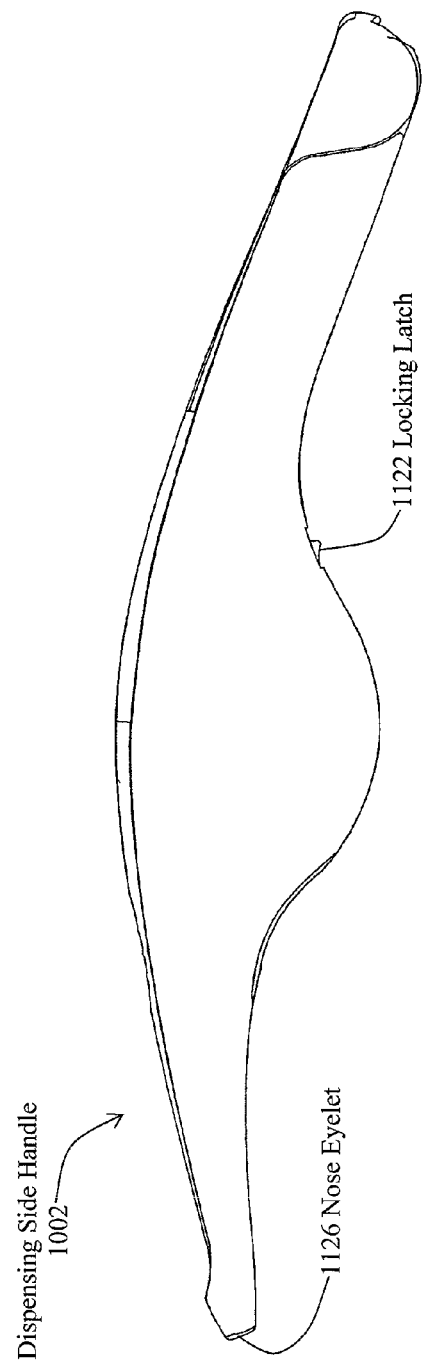
FIG. 13 is a side view of the dispensing side of the handle of FIG. 10.

FIG. 13 is an isometric side view of dispensing side handle 1002 that was shown in FIG. 10. Dispensing side handle 1002 in FIG. 13 shows nose eyelet 1126 and locking latch 1122.

Figure 14:
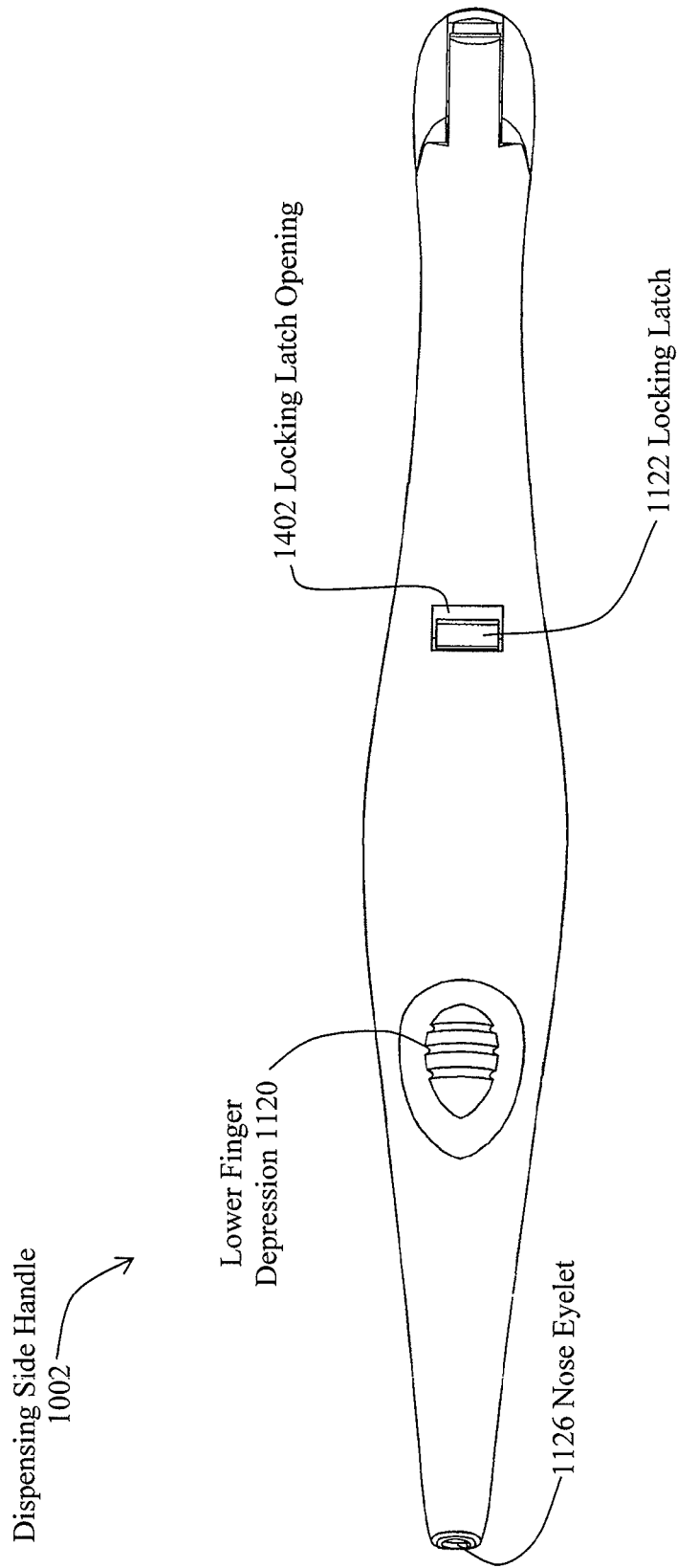
FIG. 14 is a bottom view of the dispensing side of the handle of FIG. 10.

FIG. 14 is an isometric bottom view of dispensing side handle 1002 that was shown in FIG. 10. FIG. 14 of dispensing side handle 1002 shows nose eyelet 1126, lower finger depression 1120, and locking latch 1122, that is hooked and locked onto locking latch opening 1402.

Figure 15:
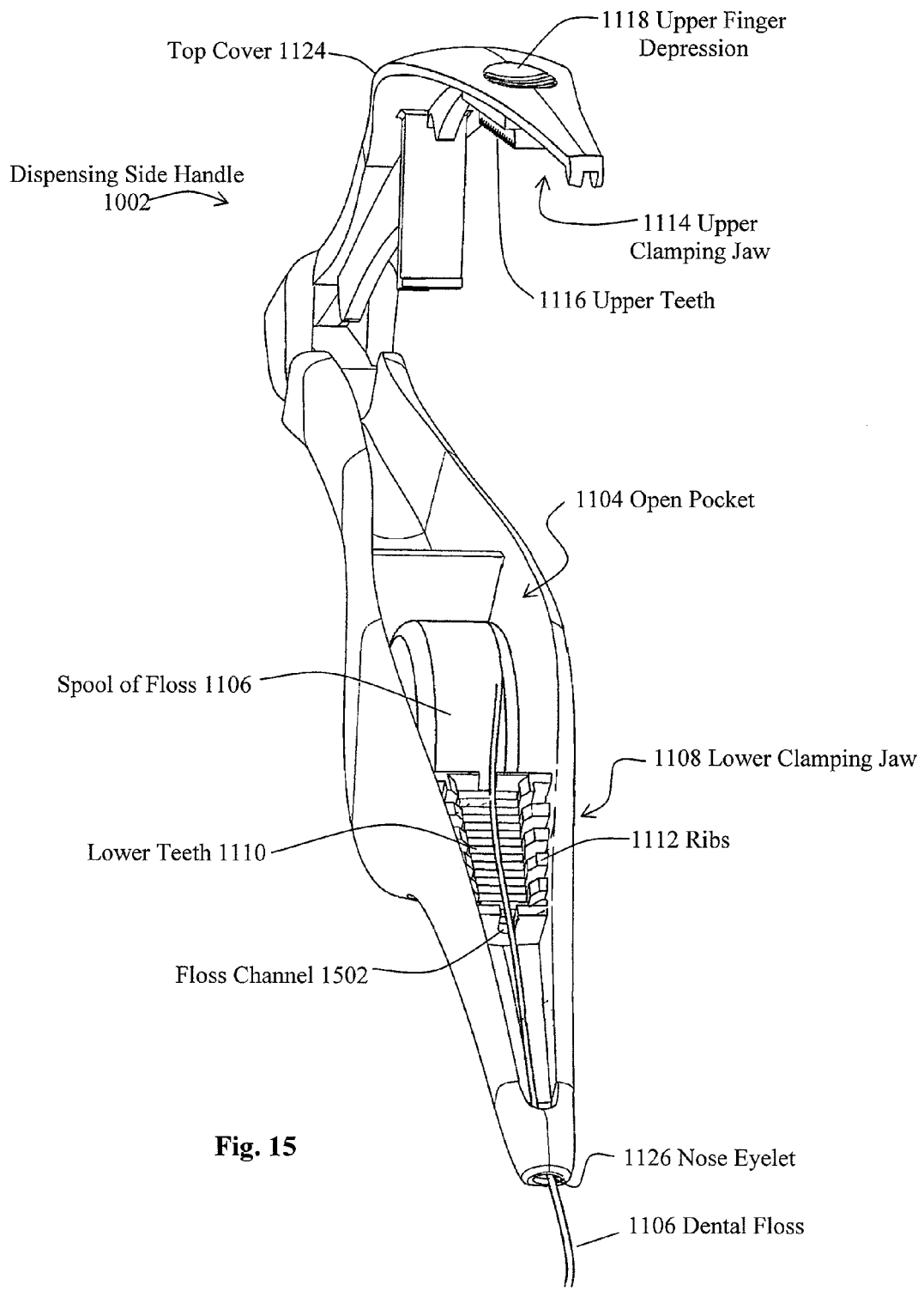
FIG. 15 is an isometric view of the dispensing side of the handle of FIG. 10.

FIG. 15 is an isometric top view of dispensing side handle 1002 that was shown in FIG. 10. Dispensing side handle 1002, in FIG. 15, shows top cover 1124 opened, so that the internal components of dispensing side handle 1002 are shown. Spool of floss 1106 is disposed in open pocket 1104, so that dental floss 1106 passes over lower clamping jaw 1108. In other words, dental floss 1106 passes over lower teeth 1110 of lower clamping jaw 1108 between ribs 1112, so that dental floss 1106 goes through floss channel 1502, through nose eyelet 1126. When top cover 1124 is closed, upper clamping jaw 1114 has contact with lower clamping jaw 1108, so that upper teeth 1116 and lower teeth 1110 create tension on dental floss 1106 when upper finger depression 1118 and lower finger depression 1120 have force applied towards each other.

Figure 16:
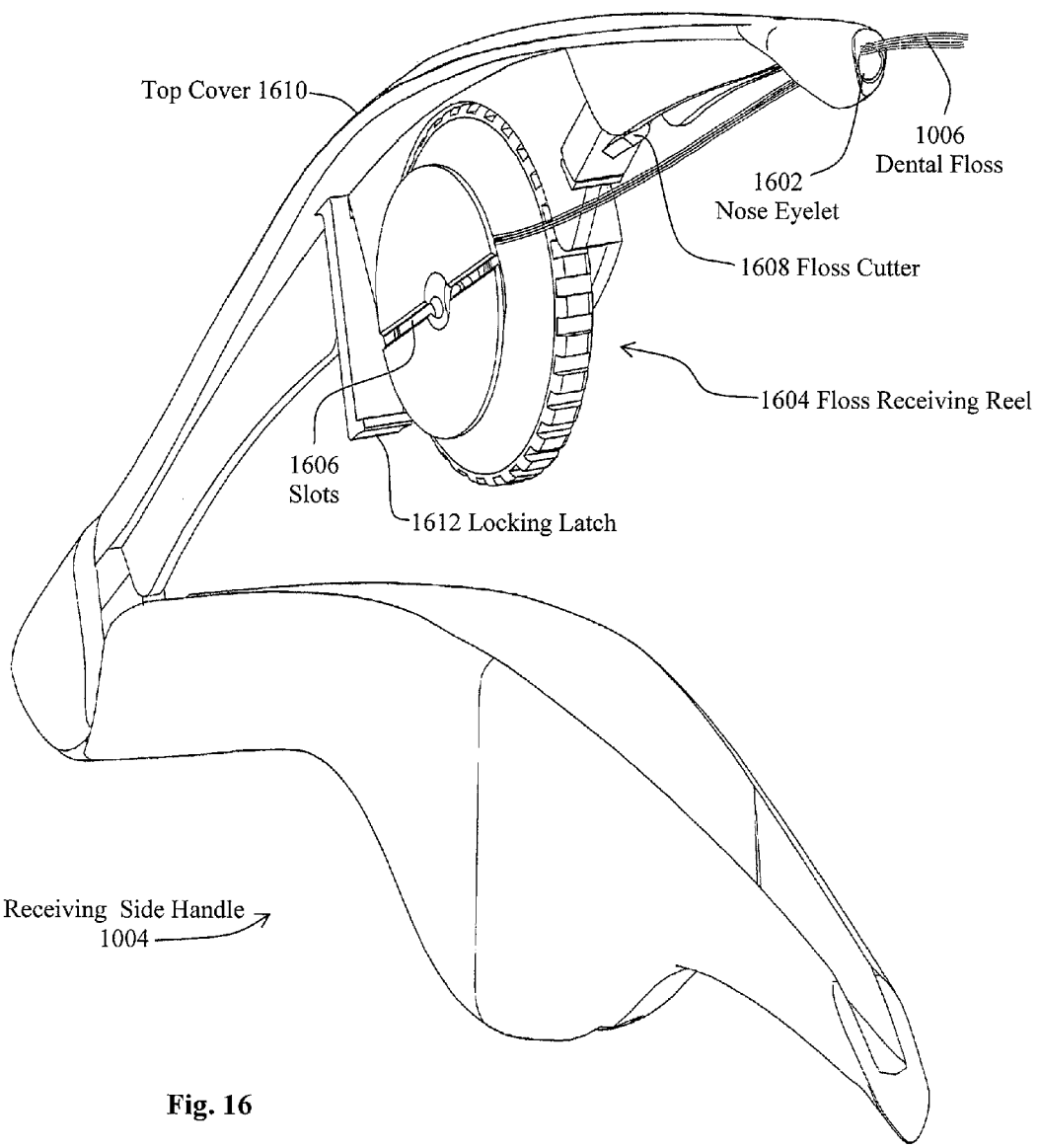
FIG. 16 is an isometric view of the receiving side of FIG. 10.

FIG. 16 is an isometric view of receiving side handle 1004 that was shown in FIG. 10. FIG. 16 shows dental floss 1006 being led through nose eyelet 1602, where dental floss 1006 is then put between slots 1606 and receiving reel 1604 is rotated in a counterclockwise direction, so that dental floss 1006 is retained on receiving reel 1604. When top cover 1610 is closed, locking latch 1612 locks into the bottom of receiving side handle 1004. When a user wants to get rid of used dental floss 1006, they can cut the used portion with floss cutter 1608.

FIG. 17 is a top view of receiving side handle 1004 that was shown in FIG. 10. FIG. 17 shows the top view of receiving side handle 1004 with nose outlet 1602.

FIG. 18 is a side view of receiving side handle 1004 showing nose eyelet 1602 and floss receiving reel 1604.

Figure 19:
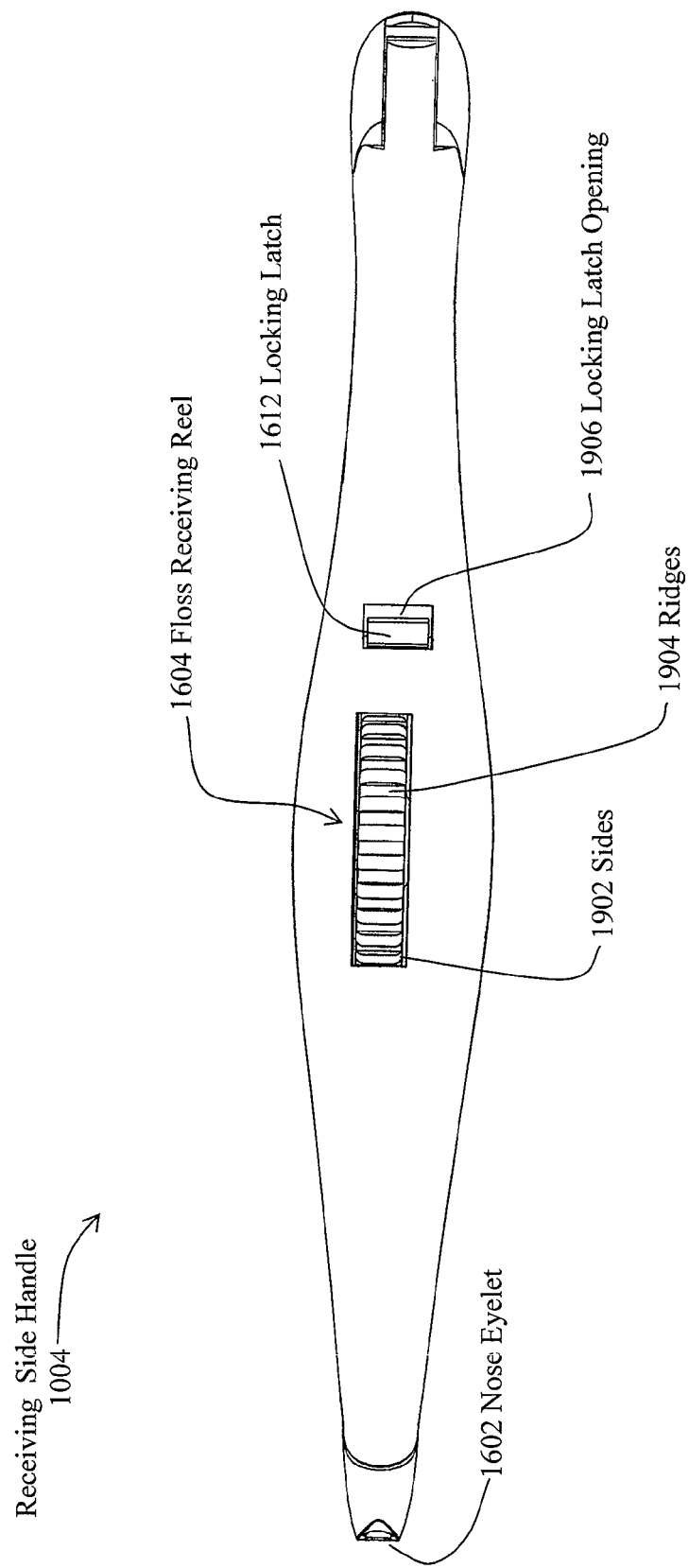
FIG. 19 is the receiving side of the handle of FIG. 10.

FIG. 19 is a bottom view of receiving side handle 1004 that was shown in FIG. 10. FIG. 19 shows nose eyelet 1602 of receiving side handle 1004 also having a receiving reel 1604 that has ridges 1904. When the receiving reel 1604 is rotated, ridges 1904 create friction on sides 1902, thereby securely receiving dental floss 1006. In other words, force is required in a rotational direction so that dental floss 1006 does not freely exit nose eyelet 1602. Locking latch 1612 is locked on locking latch opening 1906.

In addition, it should be noted that the location of the floss cutter 214 and floss cutter 1608 is not limited to a receiving side handle 104, 1104 of either embodiment and may also be located on dispensing side handle 102, 1002.

In all of the embodiments illustrated herein, a small electric motor may be used which may be coupled to finger depressors that both release and lock the floss and also activate a floss winding mechanism. Batteries, including rechargeable batteries, can be used to drive a small electric motor disposed in both the dispensing and receiving handles. In addition, magnets may be attached to the inside surface of the various embodiments of the dispensing device and receiving device of the various embodiments disclosed herein to allow both the dispensing device and receiving device to be magnetically attached to a metal plate for easy storage.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of flossing teeth comprising:
providing a dispensing side handle that dispenses dental floss;
providing a receiving side handle that receives said dental floss;
providing an upper jaw having upper teeth on an inside portion of a dispensing cover of said dispensing side handle;
providing a lower jaw having lower teeth on and inside portion of said dispensing side handle;
disposing a spool of floss in an open pocket of said dispensing side handle;
threading an end of said dental floss over said lower teeth through a floss channel having ribs and said end of said dental floss exiting at a dispensing nose eyelet;
closing said dispensing cover by engaging a locking latch opening on said dispensing cover onto a locking latch on said dispensing side handle;
providing an upper finger depression on an outside portion of said dispensing cover substantially opposite on said dispensing cover of said upper jaw located on said dispensing cover;
providing a lower finger depression under said lower jaw on said dispensing side handle so that when force is applied to said upper finger depression and said lower finger depression on said dispensing side handle, said upper teeth and said lower teeth create a tension on said dental floss;
threading said end of said dental floss into a receiving nose eyelet in said receiving side handle;
securing said end of said dental floss into a slot located on a floss receiving reel in said receiving side handle;
rotating said floss receiving reel so that said dental floss wraps around said floss receiving reel;
closing a receiving cover of said receiving side handle by engaging a locking latch on said receiving cover into a locking latch opening on said receiving side handle;
advancing said dental floss while flossing said teeth by releasing pressure on said upper finger depression and said lower finger depression on said dispensing side handle so that said floss is not under tension on said dispensing side handle while rotating said floss receiving reel so that said floss is retained in said floss receiving reel;
depressing said locking latch on said receiving side receiving side handle from said locking latch opening on said receiving side handle to open said receiving cover;
hooking said dental floss along a floss cutter of said receiving side handle, so that said dental floss is cut;
engaging said locking latch on said receiving cover into said locking latch of said receiving side handle so that said receiving cover is closed on said receiving side handle.

2. A device for flossing teeth with dental floss comprising:
a dispensing side handle that dispenses said dental floss;
a receiving side handle that receives said dental floss;
an upper jaw having upper teeth on an inside portion of a dispensing cover of said dispensing side handle;
a lower jaw having lower teeth on said dispensing side handle, so that there is an open pocket adjacent to said lower jaw where a spool of floss can be disposed;
ribs that surround said lower teeth that provide a floss channel so that said end of said dental floss is threaded over said lower teeth through said floss channel and said end of said dental floss exits at a dispensing nose eyelet in said receiving side handle;
a dispensing cover of said dispensing side handle that can be closed by engaging a locking latch opening in said dispensing cover onto a locking latch of said dispensing side handle;
an upper finger depression on an outside portion of said dispensing cover substantially opposite on said dispensing cover of said upper jaw located on said dispensing cover;
a lower finger depression under said lower jaw on said dispensing side handle, so that when force is applied to said upper finger depression and said lower finger depression on said dispensing side handle, said upper teeth and said lower teeth create a tension on said dental floss;
a receiving nose eyelet through which said dental floss is guided;
a floss receiving reel in said receiving side handle;
a slot located on said floss receiving reel so that rotating said floss receiving wheel will enable said dental floss to wrap around said floss receiving wheel;
a receiving cover that will close by engaging a locking latch on said receiving cover into a locking latch opening on said receiving side handle to allow said dental floss to be transferred from said dispensing side handle to said receiving side handle by releasing pressure on said upper finger depression and said lower finger depression on said dispensing side handle while rotating said floss receiving reel, so that said floss is retained in said receiving reel, and depressing said locking latch on said receiving side handle to disengage said locking latch from said locking latch opening on said receiving side handle to open said receiving cover, so that said dental floss can be cut on a dental floss cutter, and engaging said locking latch on said receiving side handle into said locking latch, so that said receiving cover is closed on said receiving side handle.

* * * * *